(12) United States Patent
Arquint et al.

(10) Patent No.: US 9,766,203 B2
(45) Date of Patent: Sep. 19, 2017

(54) POTENTIOMETRIC SENSOR ELEMENT AND METHOD FOR PRODUCING SAME

(71) Applicant: Hamilton Bonaduz AG, Bonaduz (CH)

(72) Inventors: Philipp Arquint, Bonaduz (CH); Fabio Sovrano, Bonaduz (CH); Karl Furger, Bonaduz (CH)

(73) Assignee: Hamilton Bonaduz AG (CH)

( * ) Notice: Subject to any disclaimer, the term of this patent is extended or adjusted under 35 U.S.C. 154(b) by 191 days.

(21) Appl. No.: 14/427,331

(22) PCT Filed: Sep. 9, 2013

(86) PCT No.: PCT/EP2013/068643
§ 371 (c)(1),
(2) Date: Mar. 11, 2015

(87) PCT Pub. No.: WO2014/040959
PCT Pub. Date: Mar. 20, 2014

(65) Prior Publication Data
US 2015/0300981 A1    Oct. 22, 2015

(30) Foreign Application Priority Data
Sep. 14, 2012   (DE) .................. 10 2012 108 636

(51) Int. Cl.
*G01N 27/416* (2006.01)
*G01N 27/28* (2006.01)
*G01N 27/36* (2006.01)

(52) U.S. Cl.
CPC ....... *G01N 27/4167* (2013.01); *G01N 27/286* (2013.01); *G01N 27/36* (2013.01)

(58) Field of Classification Search
CPC .. G01N 27/4167; G01N 27/36; G01N 27/286; G01N 27/403; G01N 27/4035; G01N 27/413
See application file for complete search history.

(56) References Cited

U.S. PATENT DOCUMENTS

2007/0110620 A1   5/2007   Pechstein et al.

FOREIGN PATENT DOCUMENTS

| DE | 100 55 090 | 5/2002 |
|---|---|---|
| DE | 102 55 741 | 6/2004 |

(Continued)

OTHER PUBLICATIONS

Machine Translation to English of DE102007008074.*
(Continued)

*Primary Examiner* — J. Christopher Ball
(74) *Attorney, Agent, or Firm* — Jansson Munger McKinley & Kirby Ltd.

(57) ABSTRACT

The potentiometric sensor element comprises a measuring element and a shield housing permanently bonded to the measuring element, in which housing an electronic sensor unit is accommodated and which is sealed off against external influences. The electronic sensor unit is connected to a contactless interface adapted to exchange energy and signals with a corresponding contactless interface in an electronic base unit. The shield housing comprises an outer sleeve and an inner sleeve, accommodated within the outer sleeve, wherein the electronic sensor unit is accommodated in the inner sleeve and is surrounded there by a first casting compound. The filled inner sleeve is in turn bonded permanently to the outer sleeve by means of a second casting compound, which is different from the first casting compound.

14 Claims, 7 Drawing Sheets

(56) References Cited

FOREIGN PATENT DOCUMENTS

| | | |
|---|---|---|
| DE | 10 2006 005 632 | 8/2007 |
| DE | 10 2007 008 074 | 8/2008 |
| DE | 10 2008 043 298 | 5/2010 |
| EP | 2 233 995 | 9/2010 |
| EP | 2233995 | 9/2010 |
| WO | 2004/102175 | 11/2004 |

OTHER PUBLICATIONS

English-language Abstract of EP 2 233 995, Arquint et al., Sep. 29, 2010.
English-language Abstract of DE 100 55 090, Pechstein et al., May 8, 2002.
English-language Abstract of DE 102 55 741, Babel et al., Jun. 9, 2004.
English-language Abstract of DE 10 2006 005 632, Blaak et al., Aug. 9, 2007.
English-language Abstract of DE 10 2007 008 074, Auerswald et al., Aug. 21, 2008.
English-language Abstract of DE 10 2008 043 298, Buschnakowski et al., May 6, 2010.

\* cited by examiner

POTENTIOMETRIC SENSOR ELEMENT AND METHOD FOR PRODUCING SAME

FIELD OF THE INVENTION

The invention pertains to a potentiometric sensor element and to a method for producing same.

BACKGROUND OF THE INVENTION

In the analysis of solutions by potentiometry, a measuring element is immersed in an analysis solution and the change in potential is determined as a function of an added reagent solution. In this way, potentiometry can be used primarily to conduct acid, base, and redox titrations. As a rule, glass electrodes are used today as the measuring element for pH measurements; such electrodes are readily available on the market.

Because moisture, dust, dirt particles, or aggressive substances can often be present in the area of the electronic parts of the sensor during potentiometric measurements, contactless signal transmission between a sensor element and a corresponding base unit was proposed in EP 1 206 012 A2, so that there are no longer any electrical contact elements—which could corrode or suffer from impaired functionality in some other way as a result of environmental influences at the transition point—between the sensor element and the base unit. According to EP 1 206 012 A2, the measuring element is permanently bonded to a shield housing, in which the electronic unit of the sensor is contained and which is sealed off against external influences. The contactless interface, which is connected to the electronic sensor unit, serves to exchange energy and signals with a corresponding contactless interface in an electronic base unit. The contactless signal transmission is effected by induction, for example.

It has been found that, even in the case of these types of sensor elements, the electronic unit of the sensor is often not protected effectively enough by the shield housing from external influences such as electromagnetic radiation. The dissipation of heat from the electronic sensor unit to the outside and leakage current between the electronic components are also problems which are still not completely solved.

It is therefore the object of the present invention to provide a potentiometric sensor element which is robust, delivers reliable measurement results under almost any set of boundary conditions, and can be manufactured in a well defined, repeatable manner, as well as to provide a corresponding method for producing the potentiometric sensor element.

SUMMARY OF THE INVENTION

The object referred to above is achieved by the apparatus and method of the invention as described and claimed herein.

According to the invention, the potentiometric sensor element comprises a measuring element and a shield housing permanently bonded to the measuring element, in which housing an electronic sensor unit is accommodated and which is sealed off against external influences. The electronic sensor unit is connected to a contactless interface, which is adapted to exchange energy and signals with a corresponding contactless interface in an electronic base unit. The shield housing comprises an outer sleeve and an inner sleeve accommodated inside the outer sleeve, wherein the electronic sensor unit is accommodated in the inner sleeve. The electronic sensor unit in the inner sleeve is surrounded by a first casting compound, so that the inner sleeve with the electronic sensor unit and the first casting compound accommodated within it forms a filled internal element of the shield housing. The filled internal element is in turn permanently bonded to the outer sleeve by means of a second casting compound which is different from the first casting compound.

A sensor element of this type is robust and can also be used for long-term measurements under almost any set of external conditions (temperature variations, corrosive environment, electromagnetic radiation fields). The electronic sensor unit is optimally protected, and at the same time it is ensured that the heat generated by the electronic components is sufficiently dissipated to the outside.

The electronic sensor element is preferably configured as a circuit board on which electronic components are mounted. This increases the compactness of the sensor element.

To improve the shielding against electromagnetic radiation, the inner sleeve of the shield housing is preferably made of a metal, a particularly preferred metal being brass.

With respect to the production method, it is especially advantageous for the inner sleeve to be configured in two parts, wherein the inner sleeve comprises a mounting part and hollow slip-over part which can be mounted on the mounting part. This facilitates the soldering of the sensor contacts of the measuring element to corresponding contacts of the electronic sensor unit with the help of the mounting part, before the hollow slip-over part is put in place.

It is especially preferred here for the electronic sensor unit to be connected to a first connecting element which engages with a second connecting element formed on the mounting part of the inner sleeve. Through the use of the first and second connecting elements, a positive-locking or friction-locking connection is produced between the electronic sensor unit and the mounting part; this connection defines the specific position which the electronic sensor unit must assume in the shield housing and in addition facilitates any necessary soldering work on the electronic sensor unit in the premounted state.

The first connecting element can, for example, be a projection, and the second connecting element can be a recess. The reverse arrangement is also conceivable. Finally, any other detachable connecting technique is also possible.

The contactless interface of the sensor element is preferably an inductive interface comprising a coil. When the inductive interface is used, it is ensured that the power supply to the electronic sensor unit from the electronic base unit and the transmission of signals from the electronic sensor unit to the electronic base unit can proceed in parallel without interference.

The coil is preferably arranged outside the inner sleeve of the shield housing and is surrounded by the second casting compound.

To obtain the desired properties of optimal support and optimal protection of the electronic sensor unit, the first casting compound is preferably selected from a group of casting compounds which offer good thermal conductivity and good electrical insulation, whereas the second casting compound is selected from a group of casting compounds which offer a thermally stable adhesive bond. Both casting compounds are preferably two-component adhesives, each of which has its own main function.

The method according to the invention for producing a potentiometric sensor element with a measuring element and a shield housing permanently bonded to it, in which housing an electronic sensor unit is accommodated and which is sealed off against external influences, comprises the following steps: providing the measuring element; arranging an inner sleeve of the shield housing around the electronic sensor unit and permanently bonding the inner sleeve to the measuring element; filling the inner sleeve with a first casting compound and curing the first casting compound, thus forming a filled inner element comprised of the inner sleeve with the electronic sensor element and the first casting compound contained within it, the first casting compound surrounding the electronic sensor unit; using a second casting compound, which is different from the first casting compound, to fill an outer sleeve of the shield housing, this sleeve being open at one end; introducing the filled internal element into the outer sleeve; and curing the second casting compound, thus permanently bonding the filled inner element to the outer sleeve of the shield housing.

This production method guarantees that air inclusions in the casting compounds are almost completely prevented and that a multi-layer structure for protecting and embedding the electronic sensor unit in the outer sleeve of the shield housing can be provided. The production method is also easy to reproduce, which means that rapid serial production is possible.

The arrangement of the inner sleeve around the electronic sensor unit and the permanent bonding of the inner sleeve to the measuring element preferably comprises the following substeps: permanently bonding a mounting part of the inner sleeve to the measuring element; mechanically coupling the electronic sensor unit to the mounting part; soldering sensor contacts of the measuring element to the electronic sensor unit; and placing a hollow slip-over part of the inner sleeve onto the mounting part and thus arranging the slip-over part around the electronic sensor unit.

The electronic sensor unit therefore takes a well-defined position within the shield housing, which further increases the reproducibility of the method; the handling of the electronic components, especially during the soldering of the measuring wires, is also facilitated.

BRIEF DESCRIPTION OF THE DRAWINGS

Additional properties and advantages of the present invention can be derived from the following description, for which purpose reference is also made to the following figures:

FIG. 5 is a cross-sectional view of a third intermediate stage during the production of a sensor element according to the invention.

DETAILED DESCRIPTION OF SPECIFIC EMBODIMENTS

Figure 1:
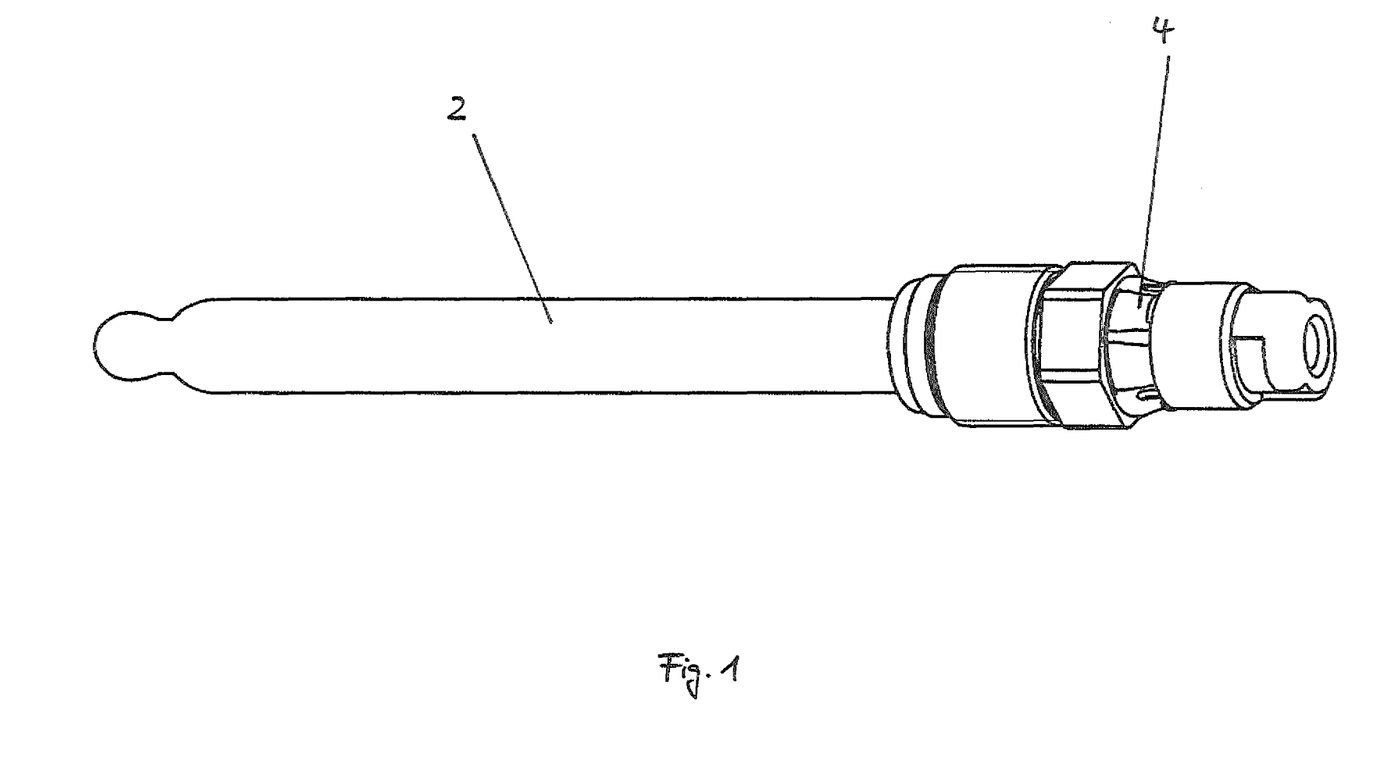
FIG. 1 is a perspective view of one embodiment of a potentiometric sensor element according to the invention.
Figure 2:
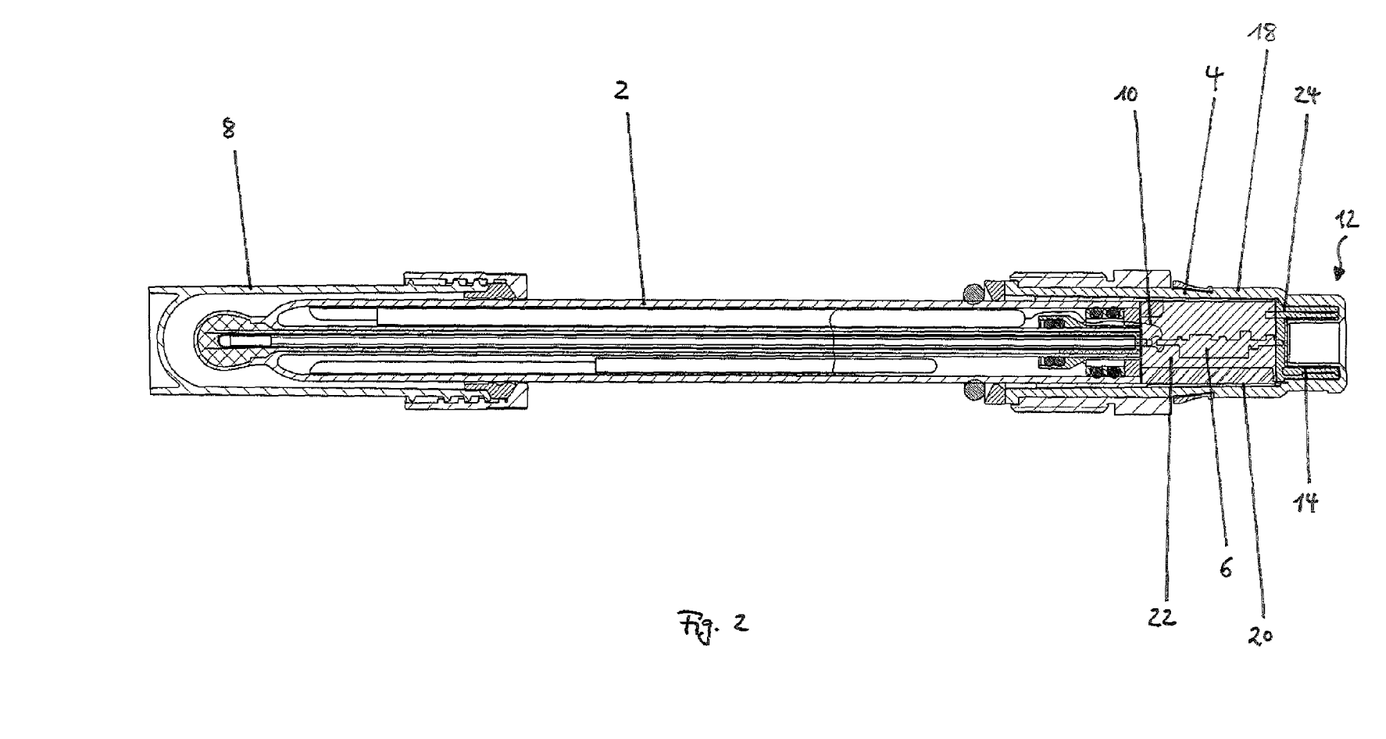
FIG. 2 is a cross-sectional through the sensor element of FIG. 1 with a protective cap placed on top.

In the present example, the potentiometric sensor element shown in FIGS. 1 and 2 is adapted to making pH measurements, but it can also be used for other types of potentiometric analysis.

The potentiometric sensor element comprises a measuring element 2 to which a shield housing 4 for an electronic sensor unit 6 is permanently bonded. Normally, the measuring element 2 is configured as a measuring rod; in this specific example, it is a conventional glass electrode. In FIG. 2, the forward end area of measuring element 2 is covered by a protective cap 8.

Shield housing 4 for electronic sensor unit 6 serves simultaneously as a mechanical connector, which is detachably connected to a corresponding base element (not shown), in which an electronic base unit is configured. The connection can be achieved by means of a bayonet joint, for example.

Electronic sensor unit 6 is preferably configured as a circuit board, on which electronic components are mounted. Electronic sensor unit 6 is connected to measuring element 2 by wires 10. Electronic sensor unit 6 is also connected to a contactless interface 12 which is adapted to exchange energy and signals with a corresponding contactless interface (not shown) in the electronic base unit (not shown). In the embodiment shown here, contactless interface 12 is an inductive interface which comprises a coil 14. In certain embodiments, coil 14 can comprise a ferrite core.

Through cooperation with a second coil (not shown), which is arranged in the electronic base unit, coil 14 effects both the transmission of the power supply signal from the electronic base unit to electronic sensor unit 6 and the transmission of the measurement signal from electronic sensor unit 6 to the electronic base unit. Details on the configuration of electronic sensor unit 6, the electronic base unit, and the corresponding transmission mechanisms can be found in paragraphs [0041]-[0044] of EP 1 206 012 A2. In addition, electronic sensor unit 6 can comprise a microprocessor, which is connected to contactless interface 12, and electronic sensor unit 6 can also comprise a digital memory.

Shield housing 4 for electronic sensor unit 6 comprises an outer sleeve 18 in which an inner sleeve 20 is contained. Outer sleeve 18 preferably has a U-shaped configuration and is longer than inner sleeve 20, which is preferably cylindrical in shape. Electronic sensor unit 6 is accommodated inside inner sleeve 20; i.e., it is radially surrounded by it. Outer sleeve 18 is preferably made of plastic, whereas inner sleeve 20 is preferably made of a metal, brass being highly preferred.

Inner sleeve 20 preferably also has a two-part configuration, as will be described below in greater detail with reference to FIGS. 3 and 5.

Electronic sensor unit 6 is surrounded by inner sleeve 20 and by a first casting compound 22, so that inner sleeve 20 with electronic sensor unit 6 accommodated inside it and the first casting compound 22 form a filled inner element of shield housing 4. This filled inner element is permanently bonded to outer sleeve 18 of shield housing 4 by a second casting compound 24, which is different from first casting compound 22.

First casting compound 22 is selected from a group of casting compounds which offer good thermal conductivity and good electrical insulation, whereas second casting compound 24 is selected from a group of casting compounds which offer a thermally stable adhesive bond.

An example of first casting compound 22 is the two-component adhesive commercially obtainable under the name "Araldite" and consisting of the resin AY 103-1 and the curing agent HY 956. There are, of course, many different types of other suitable adhesives which are well known as alternatives to the person skilled in the art.

Second casting compound 24 is, for example, the two-component adhesive commercially obtainable under the name "Araldite rapid" and comprising the resin AW 2104 and the curing agent 2934. Here, too, there are many different possibilities from which to choose.

An especially advantageous effect of the present invention is to be found in that the two casting compounds 22, 24 can be selected independently of each other and can thus have different properties. Thus, it is possible through suitable selection of first casting compound 22 to guarantee optimal heat dissipation and electrical insulation of electronic sensor unit 6, whereas the main responsibility of second casting compound 24 is to provide an adhesive bond to the outer sleeve of shield housing 4 which is as thermally stable as possible. The composition of second casting compound 24 is thus to be selected so that it is possible to compensate for the difference between the coefficient of thermal expansion of inner sleeve 20 and that of outer sleeve 18, i.e., between that of cured first casting compound 22 and that of outer sleeve 18.

Figure 7:
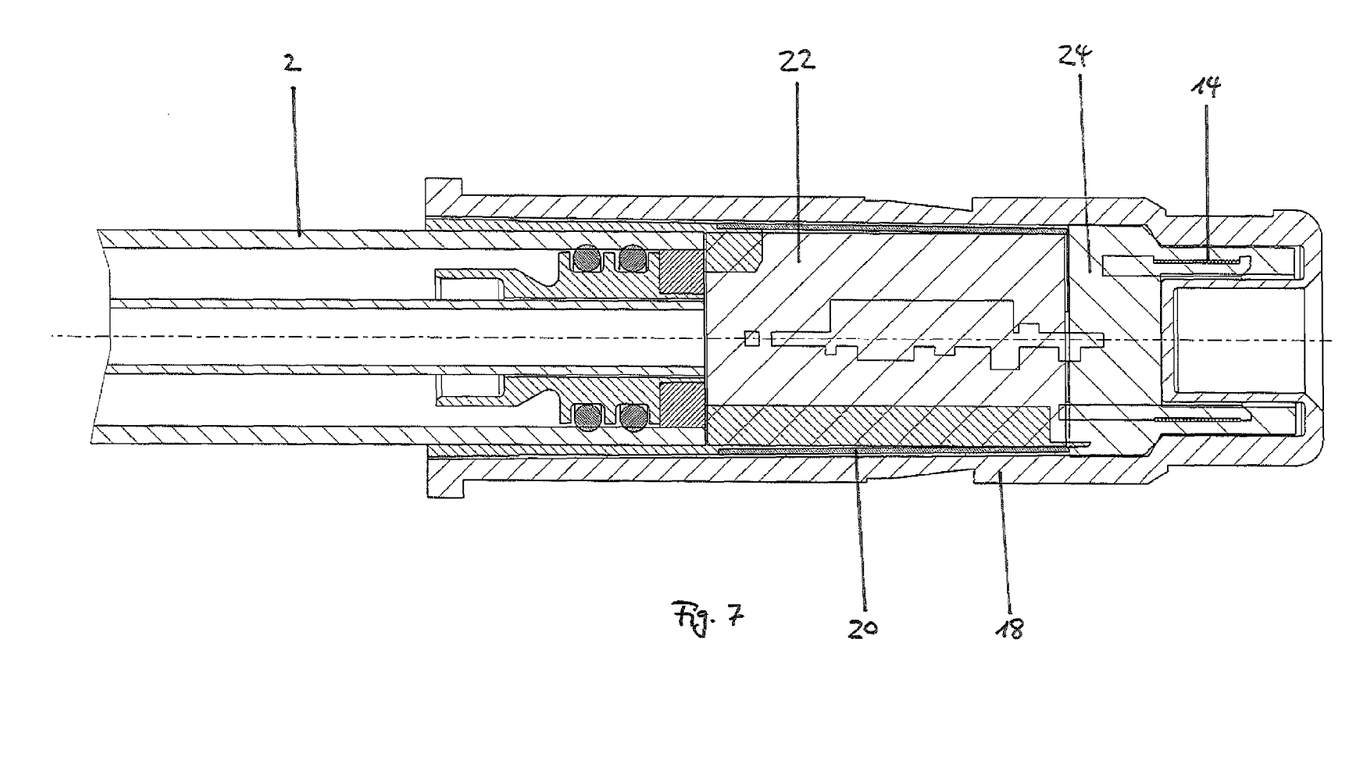
FIG. 7 is a cross-sectional view of the final stage in the production of a sensor element according to the invention.

As can be derived from FIG. 2, coil 14 projects axially out of inner sleeve 20 and is surrounded there by second casting compound 24. Second casting compound 24, furthermore, is permanently bonded to first casting compound 22 at the point where they make contact. As can be seen in FIG. 7, it is preferable for second casting compound 24 also to be present in a small gap between inner sleeve 20 and outer sleeve 18 in order to make the bond of inner sleeve 20 with outer sleeve 18 especially strong and secure. In addition, this gap between inner sleeve 20 and outer sleeve 18 offers the advantage that, while second casting compound 24 is curing, the air in this gap can escape upward, as will be described again in greater detail below in the description of the production method.

The configuration shown here is also adapted to fulfill the product guidelines of the ATEX (Explosive Atmosphere) directive. According to these guidelines, the sensor element may not be in any danger of exploding when ignitable measurement material such as various solvents, hydrogen, etc., is measured. A risk could also exist if the sensor were to heat up too much—for example, if any heat could not sufficiently dissipated from the circuit board or if a spark is generated by electrostatic charging at the head of the sensor. The entire arrangement of shield housing 4 is also immersion-proof. Finally, the air gaps and the creepage distances in the area of electronic sensor unit 6 are also clearly specified.

An example of the method according to the invention for producing the potentiometric sensor element will now be described with reference to FIGS. 3-7.

Figure 3:
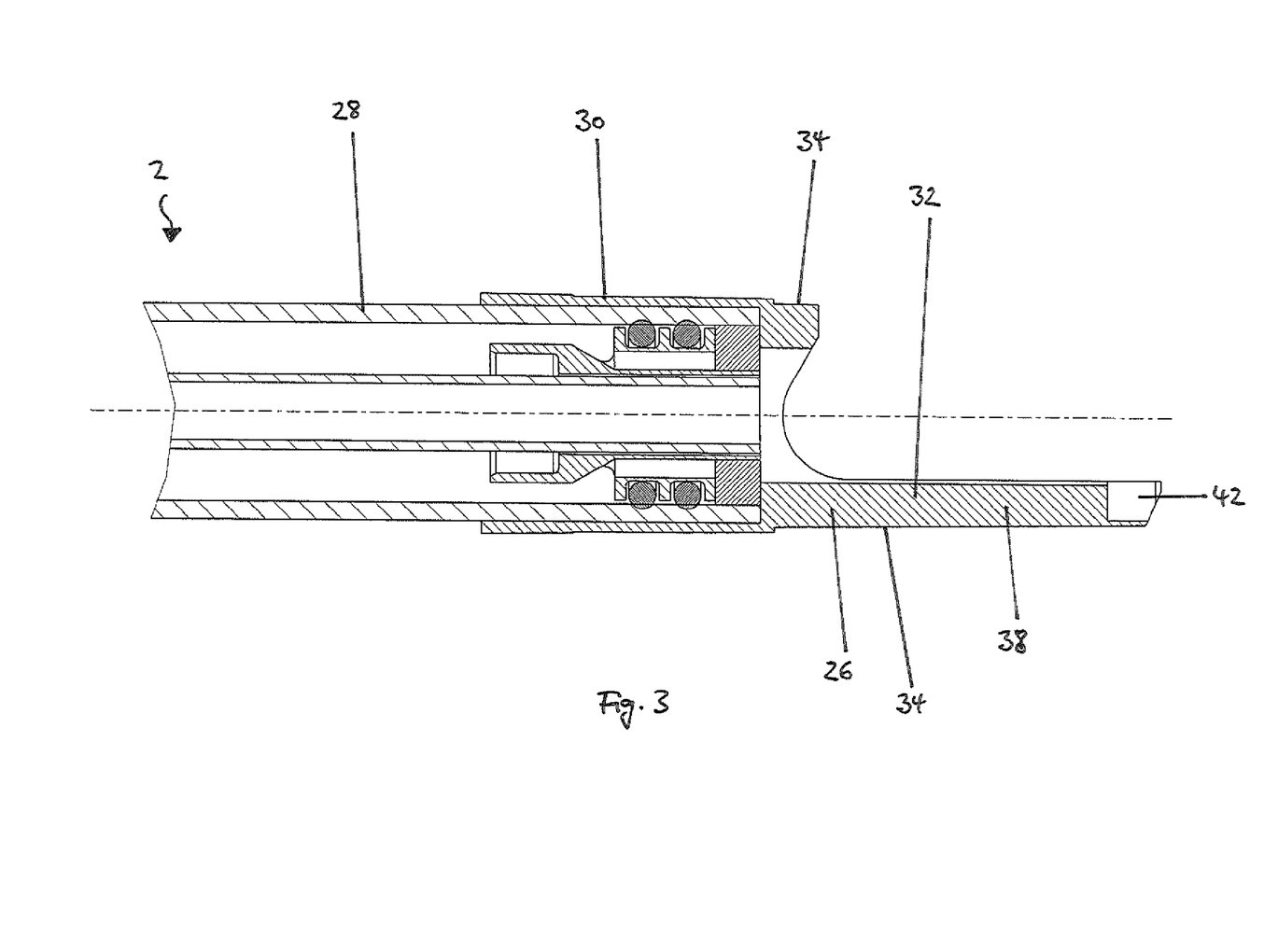
FIG. 3 is a cross-sectional view of a first intermediate stage during the production of a sensor element according to the invention.

First, as shown in FIG. 3, measuring element 2 is provided, and it is then permanently bonded to a mounting part 26 of inner sleeve 20 of shield housing 4. Expressed more specifically, the inside surface of the preferably cylindrical sleeve-like section 30 of mounting part 26 is coated with a suitable adhesive and pushed over the outside of the housing 28 of measuring element 2; in the example given here, therefore, it is pushed over the glass tube. Then the adhesive is allowed to cure.

Mounting part 26 comprises not only the sleeve-like section 30, which is pushed over measuring element 2, but also a plug-like section 32, which projects axially out from the measuring element after assembly. Plug-like section 32 extends for a certain distance around the entire circumference of mounting part 26, forming there a receiving surface 34 for the hollow slip-over part 36 of inner sleeve 20, which can be seen in FIG. 5. Around a radially limited circumferential part of sleeve-like section 30, a long arm 38 of mounting part 26 projects even farther in the axial direction from the sleeve-like section.

Figure 4:
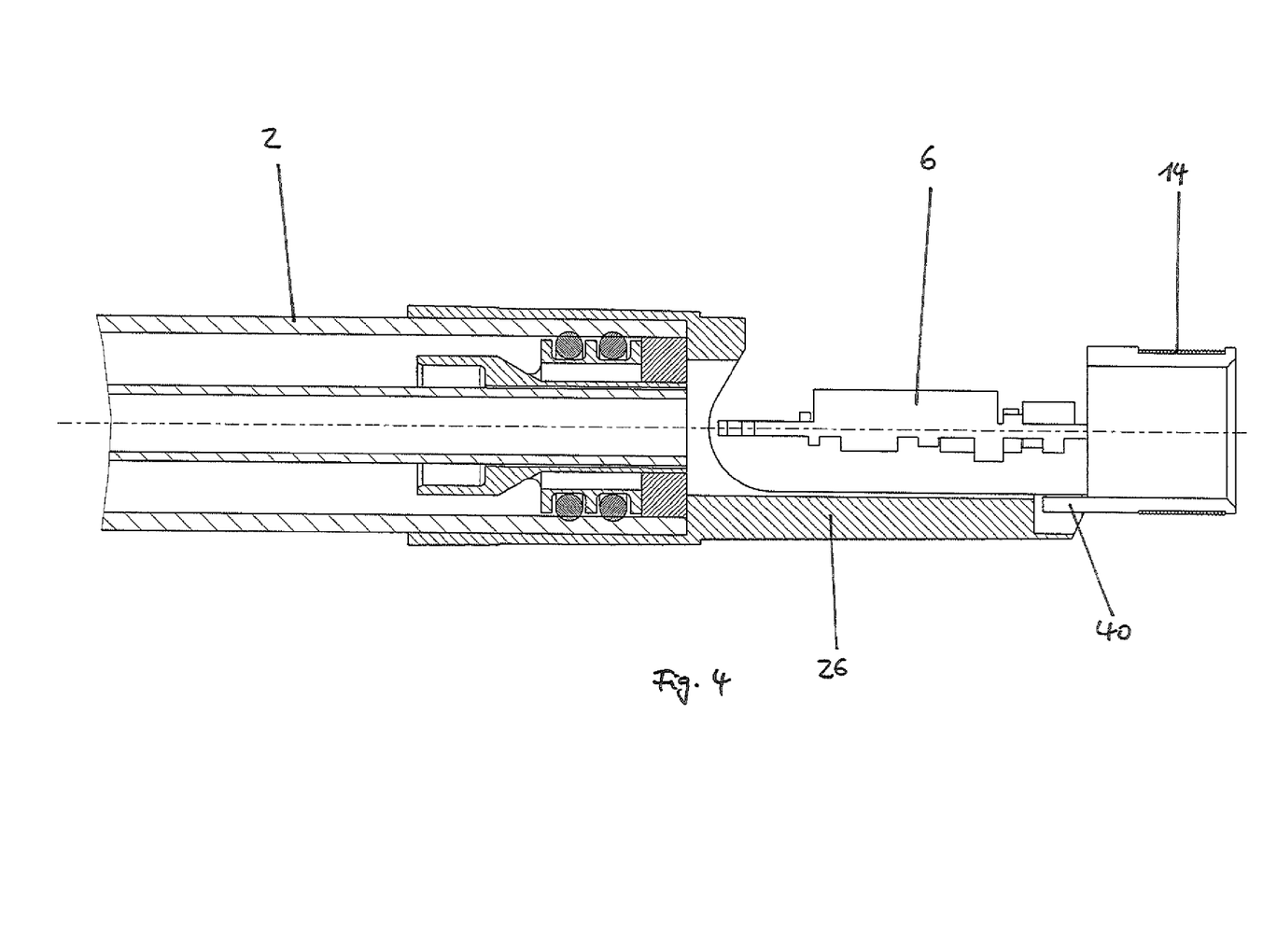
FIG. 4 is a cross-sectional view of a second intermediate stage during the production of a sensor element according to the invention.

As can be seen in FIG. 4, electronic sensor unit 6 is connected to a first connecting element 40, which, in the example shown here, is a rectangular projection which engages with a second connecting element 42 (FIG. 3), here a recess formed in arm 38 of mounting part 26 of inner sleeve 20. In the example given here, first connecting element 40 is attached to coil 14 and projects therefrom toward mounting part 26. By clipping first connecting element 40 into second connecting element 42, it is possible to couple mechanically electronic sensor unit 6 to mounting part 26. In this position, shown in FIG. 4, sensor contacts of measuring element 2 can now be soldered to electronic sensor unit 6. These contacts are in particular wires 10 shown in FIG. 2, although for the sake of clarity they are not shown in FIGS. 4-7. Alternatively, wires 10 can also be soldered to mounting part 26 before the mechanical coupling of electronic sensor unit 6 to mounting part 26. The first procedure, however, offers the advantage that electronic sensor unit 6 is supported in a defined manner during the soldering process, wherein the shape of mounting part 26 allows free access to electronic sensor unit 6.

Now, as shown in FIG. 5, the second part of inner sleeve 20, namely, slip-over part 36, is slipped over mounting part 26 and thus surrounds electronic sensor unit 6. Slip-over part 36 is in the form of a hollow body, especially preferably in the form of a cylindrical sleeve. Mounting surfaces 34 on mounting part 26 serve to support and guide slip-over part 36.

In addition to the method described above, there are also many other methods which can be used in either this or in the reverse order to arrange inner sleeve 20 of shield housing 4 around electronic sensor unit 6 and to bond it permanently to measuring element 2.

Figure 6:
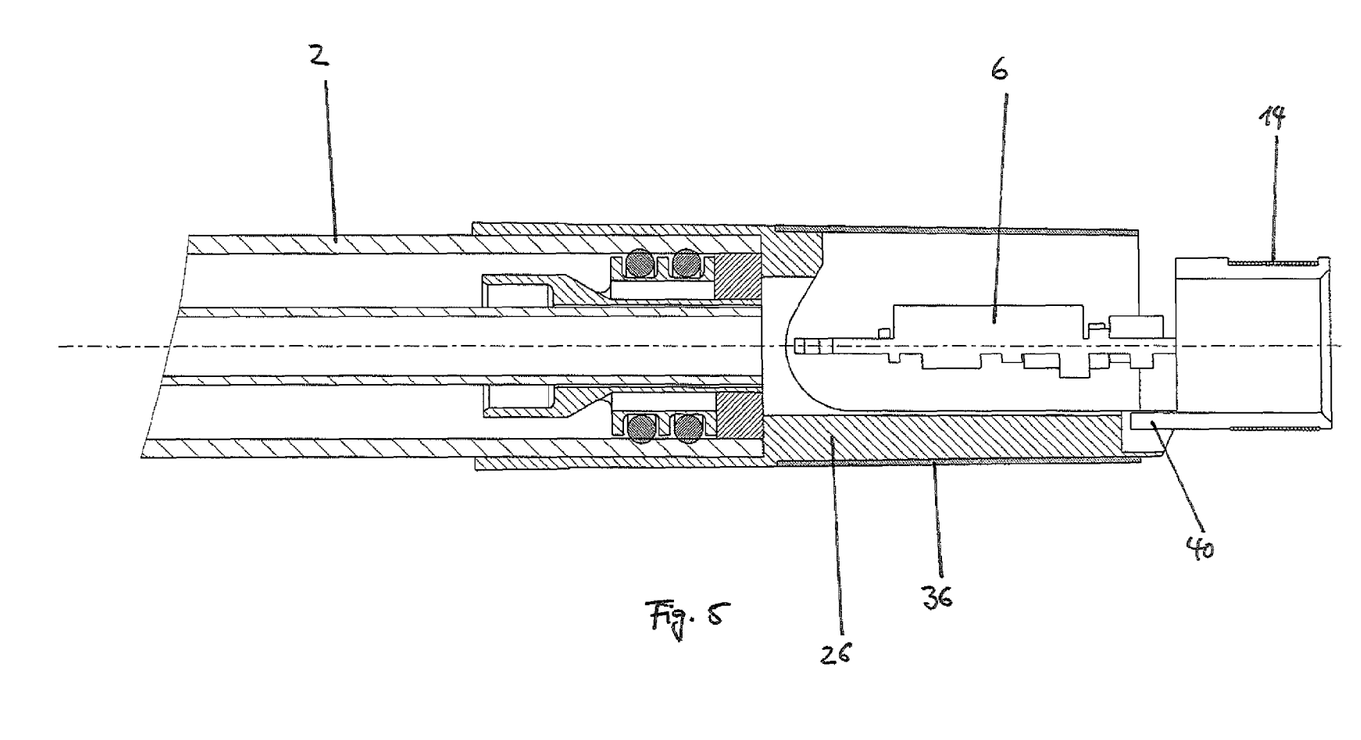
FIG. 6 is a cross-sectional view of a fourth intermediate stage during the production of a sensor element according to the invention.

Now measuring element 2 with inner sleeve 20 fastened to it is aligned vertically, and inner sleeve 20 is filled with first casting compound 22. As a result of the vertical orientation, first casting compound 22 can be brought up to the upper edge of inner sleeve 20, and it will be ensured simultaneously that air can escape upward, so that, after first casting compound 22 has cured, electronic sensor unit 6 is completely surrounded by first casting compound 22 without any air inclusions. This filled inner element, consisting of inner sleeve 20, first casting compound 22, and electronic sensor unit 6, is shown in FIG. 6.

Finally, outer sleeve 18, which has an essentially U-shaped configuration, is held in a vertical position with the opening facing upward and is partially filled with second casting compound 24. Then the filled inner element is introduced from above with coil 14 facing downward. It is preferable for an air gap to remain between the filled inner element, i.e., measuring element 2, and outer sleeve 18, through which gap air can escape during the curing of second casting compound 24. In addition, this air gap is filled by the rising second casting compound 24. It is important here that the correct quantity of second casting compound 24 be used. First, the quantity must be large enough to ensure a reliable bond between the filled inner element and outer sleeve 18, i.e., between coil 14 and outer sleeve 18. Conversely, it is absolutely imperative to avoid any overflow resulting from an excessive quantity of second casting compound 24. After second casting compound 24 has cured, the filled inner element is permanently bonded to outer sleeve 18 of shield housing 4.

The invention claimed is:
1. A potentiometric sensor element comprising:
a measuring element; and
a shield housing permanently secured to the measuring element and accommodating an electronic sensor unit therein sealed off against external influences, wherein:
the electronic sensor unit is connected to a contactless interface adapted to exchange energy and signals with a corresponding contactless interface in an electronic base unit;
the shield housing includes an outer sleeve and an inner sleeve accommodated in the outer sleeve, the electronic sensor unit being within the inner sleeve and surrounded by a first casting compound such that the inner sleeve with the electronic sensor unit and first casting compound form a filled inner element of the shield housing; and
the filled inner element is permanently bonded to the outer sleeve by a second casting compound which is different from the first casting compound.

2. The potentiometric sensor element of claim 1 wherein the electronic sensor unit is configured as a circuit board with electronic components mounted thereon.

3. The potentiometric sensor element of claim 2 wherein the inner sleeve of the shield housing is made of a metal.

4. The potentiometric sensor element of claim 3 wherein the inner sleeve of the shield housing is made of brass.

5. The potentiometric sensor element of claim 1 wherein the inner sleeve of the shield housing is made of a metal.

6. The potentiometric sensor element of claim 5 wherein the inner sleeve of the shield housing is made of brass.

7. The potentiometric sensor element of claim 1 wherein the inner sleeve is configured in two parts, including a mounting part and a hollow slip-over part mountable on the mounting part.

8. The potentiometric sensor element of claim 7 wherein the electronic sensor unit is connected to a first connecting element engaged with a second connecting element formed on the mounting part of the inner sleeve.

9. The potentiometric sensor element of claim 8 wherein the first connecting element is a projection and the second connecting element is a recess.

10. The potentiometric sensor element of claim 1 wherein the contactless interface is an inductive interface including a coil.

11. The potentiometric sensor element of claim 10 wherein the coil is arranged outside the inner sleeve and is surrounded by the second casting compound.

12. The potentiometric sensor element of claim 1 wherein:
the first casting compound is selected from a group of casting compounds characterized as having good thermal conductivity and providing good electrical insulation; and
the second casting compound is selected from a group of casting compounds characterized as providing a thermally-stable adhesive bond.

13. A method for producing a potentiometric sensor element having a measuring element and a shield housing permanently secured thereto, the shield housing accommodating an electronic sensor unit therein sealed off against external influences, comprising the steps of:
providing the measuring element;
arranging an inner sleeve of the shield housing around the electronic sensor unit and permanently bonding the inner sleeve to the measuring element;
filling the inner sleeve with a first casting compound and curing the first casting compound thereby to form a filled inner element comprised of the inner sleeve with the electronic sensor unit and first casting compound accommodated within it, the first casting compound surrounding the electronic sensor;
using a second casting compound different from the first casting compound to fill an outer sleeve of the shield housing, the outer sleeve being open at one end;
introducing the filled inner element into the outer sleeve; and
curing the second casting compound to thereby permanently bond the filled inner element to the outer sleeve.

14. The method of claim 13 wherein the arranging of the inner sleeve around the electronic sensor unit and the permanent bonding of the inner sleeve to the measuring element comprise the following steps:
permanently bonding a mounting part of the inner sleeve to the measuring element;
mechanically coupling the electronic sensor unit to the mounting part;
soldering sensor contacts of the measuring element to the electronic sensor unit; and
placing a hollow slip-over part of the inner sleeve onto the mounting part thereby to arrange the slip-over part around the electronic sensor unit.

* * * * *